(12) United States Patent
Mansy et al.

(10) Patent No.: US 6,595,928 B2
(45) Date of Patent: Jul. 22, 2003

(54) METHOD AND APPARATUS FOR DETECTION OF AIR CAVITIES IN A BODY

(75) Inventors: Hussein A. Mansy, Chicago, IL (US); Richard H. Sandler, Evanston, IL (US)

(73) Assignee: Rush-Presbyterian-St. Luke's Medical Center, Chicago, IL (US)

( * ) Notice: Subject to any disclaimer, the term of this patent is extended or adjusted under 35 U.S.C. 154(b) by 0 days.

(21) Appl. No.: 10/164,106

(22) Filed: Jun. 5, 2002

(65) Prior Publication Data
US 2002/0151789 A1 Oct. 17, 2002

Related U.S. Application Data

(63) Continuation of application No. 09/050,716, filed on Mar. 30, 1998, now abandoned.

(51) Int. Cl.[7] .................................................. A61B 5/08
(52) U.S. Cl. ........................ 600/529; 600/552; 600/586
(58) Field of Search .............................. 600/407, 529, 600/586, 437, 438, 552, 595

(56) References Cited

U.S. PATENT DOCUMENTS

| | | | | |
|---|---|---|---|---|
| 4,008,711 A | * | 2/1977 | Olinger et al. | 600/371 |
| 4,672,977 A | * | 6/1987 | Kroll | 600/528 |
| 4,689,986 A | * | 9/1987 | Carson et al. | 73/19.03 |
| 4,928,697 A | * | 5/1990 | Hsu | 600/402 |
| 5,165,417 A | * | 11/1992 | Murphy, Jr. | 600/549 |
| 5,259,384 A | * | 11/1993 | Kaufman et al. | 600/442 |
| 5,309,922 A | * | 5/1994 | Schechter et al. | 600/534 |
| 5,701,912 A | * | 12/1997 | Greening et al. | 600/586 |
| 5,718,227 A | * | 2/1998 | Witlin et al. | 600/528 |
| 5,816,245 A | * | 10/1998 | Manseur et al. | 128/664 |
| 6,443,907 B1 | * | 9/2002 | Mansy et al. | 600/529 |

OTHER PUBLICATIONS

Wodicka et al. "Spectral characteristics of Sound Transmission in the Human Respiratory System" 1990 IEEE Transactions on Biomedical Engineering vol. 37 No. 12 pp. 1130–1135.*

Wodicka et al. "Transfer Function of Sound Transmission in Subglottal Human Respiratory System at Low Frequencies" 1990 American Physiological Society pp. 2126–2130.*

Goncharoff et al. "Wideband Acoustic Transmission of Human Lungs" 1989 Medical & Biological Engineering & Computing pp. 513–519.*

* cited by examiner

Primary Examiner—Ruth S. Smith
(74) Attorney, Agent, or Firm—Fitch, Even, Tabin & Flannery

(57) ABSTRACT

A method and apparatus for detecting the presence of gas cavities in the abdomen, the thorax and elsewhere is disclosed. The apparatus includes an actuator for transmitting low frequency vibro-acoustic waves (such as from a white noise generator, impulse wave or chirp signal) into the body at a first location and a detector (such as from a vibro-acoustic sensor, microphone, air-coupled microphone or optical detector) for receiving the transmitted low frequency vibro-acoustic waves at a second location on the body. The actuator and detector are positioned to be effective for detecting the suspected gas cavity. The detector generates a response signal which is analyzed. Resonance waves and anti-resonance waves in the detected signal indicate the presence of a gas cavity.

19 Claims, 8 Drawing Sheets

METHOD AND APPARATUS FOR DETECTION OF AIR CAVITIES IN A BODY

This is a continuation of prior application Ser. No. 09/050,716, filed Mar. 30, 1998, now abandoned, which is hereby incorporated herein by reference in its entirety.

BACKGROUND OF THE INVENTION

This invention relates to a method and apparatus for detecting air cavities, such as pneumothorax and pneumoperitoneum, in humans and animals. Pneumothorax is the state in which air or other gas is present in the pleural cavity and which occurs spontaneously as a result of disease or injury of lung tissue or puncture of the chest wall. Pneumoperitoneum is the state in which air or other gas is present in the peritoneal cavity.

Pneumothoraces are commonly encountered as a spontaneous process, an iatrogenic complication, or secondary to traumatic injuries. Air pressure in the pleural space may increase leading to tension pneumothoraces requiring prompt diagnosis and treatment. Pneumothorax diagnosis often requires radiographic confirmation since history and physical examination findings can be non-specific. Valuable time may be lost while waiting for chest x-ray results and even after they are obtained, interpretation can be uncertain or incorrect.

Spontaneous pneumoperitoneum (free air in the abdomen) results from a hole in the wall of the GI tract. Detection in the setting of acute abdominal symptoms is important since most such cases require emergency surgery. The most common causes of pneumoperitoneum are perforated gastric or duodenal ulcer or colonic perforation secondary to mechanical obstruction, infection, infarction, severe ileus, ulcerated carcinoma or trauma.

Gastrointestinal perforation (GIP) is a common condition resulting from either trauma or progression of ulcerating, inflammatory, ischemic, or mechanically obstructing diseases of the gastrointestinal (GI) tract. It is estimated that there are from 10,000 to 70,000 cases in the United States each year. Much higher rates of GIP would be expected in regions of armed conflict or poor medical care. High morbidity or mortality rates accompany those abdominal catastrophes, as spillage of microbial, enzyme and other intraluminal contents into the peritoneum typically cause rapid disease advancement and often death if proper initiation of medical and surgical treatment is delayed. Ready access to a low cost and safe technology that would immediately identify GIP would save many lives-each year. Currently, GIP is diagnosed preoperatively by imaging of free intraperitoneal air.

Several techniques exist to diagnose GIP and pneumoperitoneum, including radiographs, computerized tomography (CT) examination and ultrasound. Each technique has limitations of availability, cost or accuracy. For example, meticulously performed plain radiographs with the patient positioned in the upright or left lateral decubitus (left side down) positions for ten to twenty minutes reportedly can detect small amounts of intraperitoneal gas. However, it is uncommon for ill patients with acute abdominal pain to be kept in those positions, at least for more than a brief period. Therefore, supine (lying on the back) radiographs are the most commonly obtained tests for pneumoperitoneum. Although a recent review suggests several ways to improve diagnostic accuracies, typical pneumoperitoneum detection sensitivities are less than 60%.

Although availability, cost and time delays may limit utility, CT examination is currently the most sensitive and specific tool for diagnosing intraperitoneal gas. Careful studies demonstrate that CT is capable of reliably detecting even minute amounts of air. The superiority of CT is striking when compared to a sensitivity of only 38% for upright radiographs. The accuracy of ultrasound imaging may be similar to plain radiography, but more studies are required to confirm its precise utility. Ultrasound and CT scanning, though accurate, are more expensive than radiographs and often unavailable in a timely manner. This is especially true in remote areas, such as rural regions, battlefield settings or in developing nations.

Researchers have applied the technique of external low-frequency vibro-acoustic excitation and response measurements to the diagnosis of other biological conditions. For example, Wodicka et al., "Spectral Characteristics of Sound Transmission in the Human Respiratory System," *IEEE Transactions of Biomedical Engineering,* Vol. 37, No. 12, December 1992, pp. 1130–35, Wodicka et al., "Transfer function of sound transmission in subglottal human respiratory system at low frequencies," *The American Physiological Society,* 1990, pp. 2126–2130, and V. Goncharoff, "Wideband acoustic transmission of human lungs," *Med. & Biol. Eng. & Comput.,* 27, 1989, pp. 613–619 have studied the acoustic transmission properties from the trachea to the chest wall. They found that sound transmission times were frequency dependent as different wavelengths of sound coupled to different parts of the lung lining, principally due to geometrical changes. While these studies offer some relevant information regarding types of indices which can be used for analysis and types of transducers, there are many issues specific to the abdomen as opposed to the chest and lungs due to the great differences in their structures.

Several researchers have led efforts in the utilization of low frequency vibro-acoustic excitation, i.e., 20 to a few hundred Hertz, coupled with doppler ultrasonic imaging, which is sometimes referred to as sonelastic imaging. This technique has been proposed to locate tumors which produce significant changes in stiffness properties in an otherwise acoustically homogeneous region. The presence of the tumor, or localized stiffness, will distort the resonant shapes of vibration patterns caused by low frequency excitation. These patterns can be imaged using the very expensive laser doppler vibrometry.

Accordingly, there is a need for an accurate, low cost, portable technology capable of diagnosing GIP, pneumothorax and pneumoperitoneum with minimum discomfort to the patient.

SUMMARY OF THE INVENTION

To achieve the foregoing and other objects and in accordance with the principles of the invention, a low cost, painless and safe method and apparatus for diagnosing patients with gastrointestinal perforation is described.

The underlying physics principles employed in the invention are similar to those used during chest percussion in which the hyperresonance often associated with large pneumothoraces is a manifestation of bioacoustic changes. Low frequency vibro-acoustic properties of the abdomen depend on the abdominal contents and free (extraluminal) air produces measurable differences in the vibro-acoustic response. Thus, if known excitations are applied to the abdomens of perforated patients, response differences are detectable by a vibro-acoustic sensor.

An apparatus for detecting the presence of a gas cavity in the thorax, abdomen, peritoneal cavity and elsewhere in a body includes an actuator for transmitting a source of vibro-acoustic waves into a first location. The actuator introduces a standardized audible sound, gently, into the chest wall. A white noise generator producing vibro-acoustic waves in the range of 5 Hz to 2000 Hz is generally desirable. Electromagnetic shakers and speakers may also be used in place of the actuator. A detector or acoustic sensor, such as an air-coupled microphone (electronic stethoscope), is placed at a second location for detecting the transmitted vibro-acoustic waves. The detector detects changes in the chest wall caused by the presence of an air cavity and generates a signal representative of the frequency response of the chest cavity. Preferably, the actuator and detector are positioned on the body at locations effective for detecting the suspected air cavity. For a supine subject, this would be in the most anterior position. The level of the third rib may be chosen in human subjects to avoid the diaphragm. Indeed, during the detection phase, the operator can move the detector to different locations to test for the largest peaks (resonance) and dips (anti-resonance) in the response signal. A processor analyzes the frequency response of the detected signal for the presence of resonance waves and anti-resonance waves and other acoustic property changes, which are indicative of chest cavity changes. A gas cavity is detected when the frequency response shows a peak, indicative of a resonance wave, followed by a dip, indicative of an anti-resonance wave.

Several types of detectors (transducers) may be used: vibro-acoustic sensors, microphones, air-coupled microphones and optical detectors. For optimal coupling to the skin surface, the measurement sensor's dynamic impedance should match that of the skin surface. It has been found that lower signal to noise ratios were observed for air coupled sensors at high frequencies. The response of air coupled microphones was found to be sensitive to the size and geometrical shape of the coupling surface. Impedance matched accelerometers have been used in place of microphones in some studies of the, abdominal region.

BRIEF DESCRIPTION OF THE DRAWINGS

FIG. 16 is a block diagram of a computer and associated hardware shown in FIG. 4a.

DETAILED DESCRIPTION OF THE PREFERRED EMBODIMENTS

A pneumothorax condition involves the presence of an enclosed volume of free air located between the chest wall and the lung parenchyma, specifically between the visceral and parietal pleura. The acoustic behavior of this air volume is extremely different from either the chest wall or the parenchyma itself. At frequencies below 10 kHz, where sound wavelengths significantly exceed alveolar size, the lung parenchyma acts like a foam-like substance that is a homogeneous mixture of air and soft tissue. At these low frequencies, predominantly compression wave propagation is supported. With the composite density dominated by the tissue-component, and the composite stiffness by the air, the resulting speed of sound is very low, 25–70 meters per second. This is very different from the free air compression wave sound propagation speed of roughly 330 meters per second.

Low audible frequency wave propagation in the subglottic region is strongly damped with minimal resonant behavior, and has a greatly attenuated response with increasing frequency above a few hundred Hz. On the other hand, a pneumothorax free air volume will have relatively minimal acoustic damping and exhibit a resonant response to excitation. Resonant frequencies will depend on pneumothorax size and boundary (chest wall and parenchyma) conditions. Another expected acoustic change with pneumothorax is an increase in high frequency sounds, due to reduced damping and inertia directly beneath the chest wall. This effect has been noted by skilled physicians as "hyperresonance" during physical examination by percussion. Thus a consequence of pneumothorax is that the audible frequency dynamic response of the thorax is altered due to the presence of an enclosed air volume.

Detection of free gas in the abdomen using low frequency vibro-acoustic excitation (5–2000 Hz) was tested by researchers at the Rush Medical College on three mongrel dogs. Sedated animals were placed in the supine position and a white noise source (the "stinger" of an electromagnetic shaker driven by an amplifier and a signal generator) was placed on the right flank while an electronic stethoscope measured the signal at five equally spaced surface points located in the same vertical plane as the excitation point and spanning the area from the left to the right flanks. The shaker input signal contained all frequencies in the operating range, with uniform amplitude within 5%. The shaker output vibration was measured by an accelerometer attached to the stinger. Starting with no free gas, varying amounts of carbon dioxide were injected into the abdominal cavity through a surgically installed catheter. Carbon dioxide was used because of its similarity to air and its better absorption into the body.

Figure 1A:
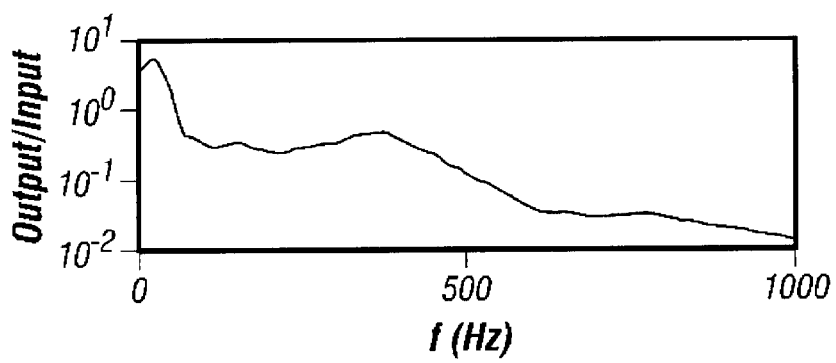
FIGS. 1a and 1b show the typical frequency response measured at the abdominal wall of a dog for a white noise input.
Figure 1B:
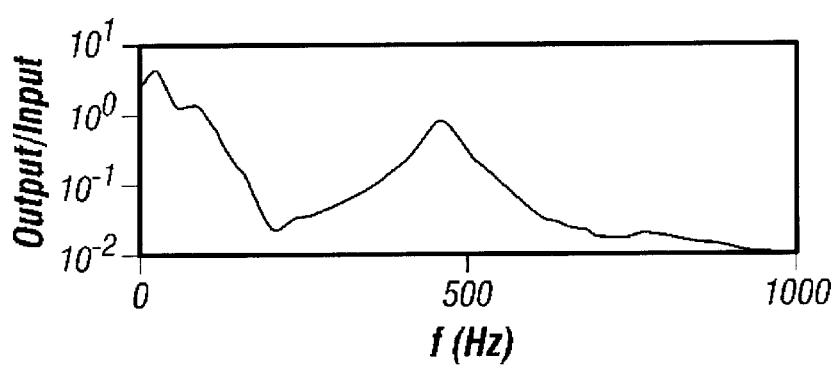

The spectra at the detection points were estimated and normalized by that of the input vibration (shaker output). FIG. 1a shows a typical spectrum for a sensor placed midline in a normal animal. The frequency dependent response is clear. After an initial decrease in amplitude with increasing frequency, the amplitude reached a plateau (for frequency, f=70–400 Hz). Then it continued to decrease for frequencies greater than 400 Hz. Consistent spectral changes were detected when free gas was introduced. FIG. 1b shows a typical spectrum at the midline of an animal with 500 ml of free gas. Strong resonance (at 470 Hz) and anti-resonance (at 210 Hz) in the system response are evident which may be associated with the gas chamber resonances discussed below. These frequencies were shifted downward slightly as the amount of gas increased due to the increased size of the gas pocket, which decreased its resonance frequency.

Figure 2A:
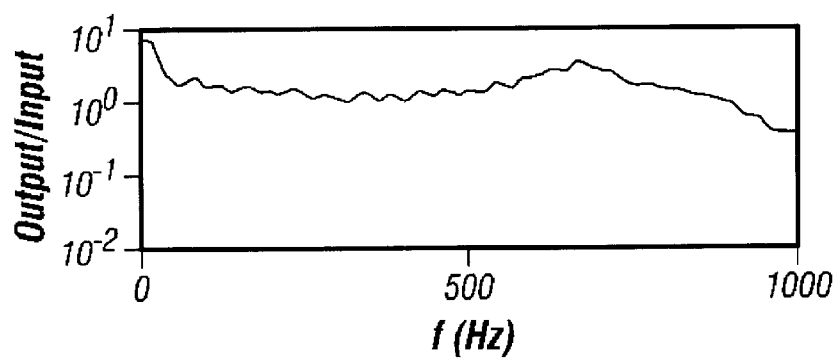
FIGS. 2a and 2b show the typical frequency response measured at the balloon surface for a white noise input.
Figure 2B:
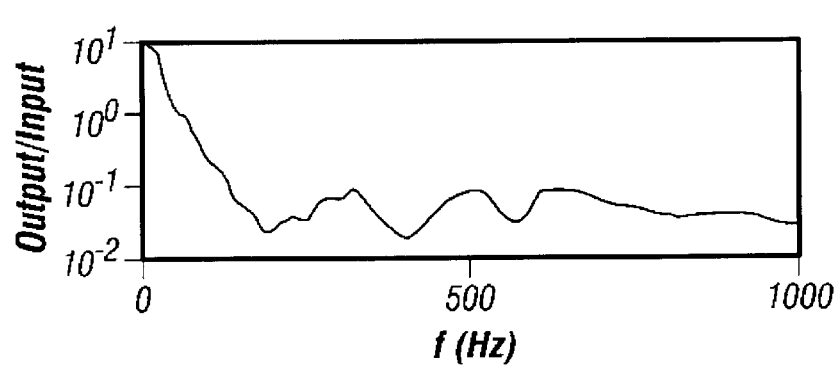

To investigate the feasibility of using a simple mechanical model in the representation of the underlying mechanisms of vibro-acoustic wave transmissions in the abdomen, experiments with balloon models were carried out. The conditions in the animal experiment were approximated by a balloon containing a fixed amount of water and variable amounts of gas. A striking, similarity in the frequency dependent response to that of the animal experiment can be seen. A plateau in the spectrum between 100 and 800 Hz was found when gas was absent as shown in FIG. 2a. A series of resonances and anti-resonances appeared in the spectrum when gas was injected into the balloon as shown in FIG. 2b. Further pilot balloon experiments have shown that these results are sensitive to excitation source and the detection point location. For example, best gas detection was achieved when the sensor was closest to the gas pocket. The excitation source location was found to be less critical although the system performance also improved when the excitation source location was closer to the pocket. By proper placement of source and sensor, as little as 1–2 ml of gas was detectable using this method.

Figure 3A:
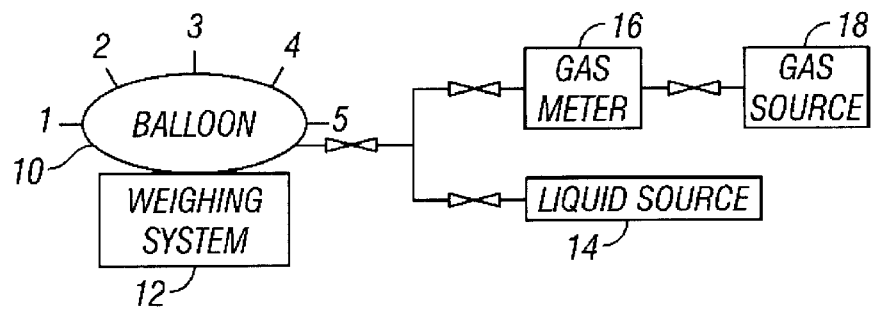
FIGS. 3a and 3b show the experimental setup for balloon filling and vibro-acoustic testing.

A schematic of the basic setup used is shown in FIG. 3. Referring to FIG. 3a, a balloon 10 was filled with an initial amount of liquid from liquid source 14. The amount of liquid was determined by weighing using weighing system 12. Gas from gas source 18 was metered through gas meter 16 into balloon 10. To avoid stress on the balloon, liquid was metered off as the amount of gas was increased. Five proposed sensor locations are indicated schematically by elements 1–5.

Figure 3B:
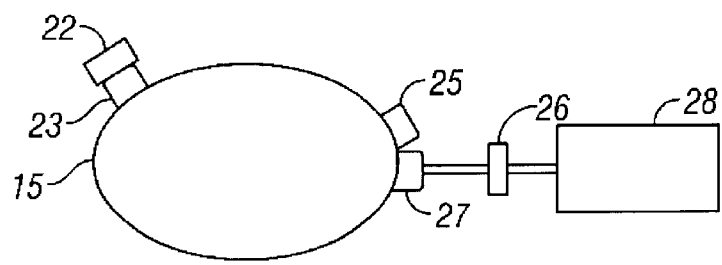

Referring to FIG. 3b, two sensors, 23 and 25 were placed at different locations on subject 15. Vibration source 28 was connected to load cell 26 which provided an input signal to actuator 27, which generated vibro-acoustic waves. Vibratory response is detected at sensor 23, coupled to load cell 22. An additional sensor 25 may be connected to another load cell for detecting vibro-acoustic response at its location.

Figure 4A:
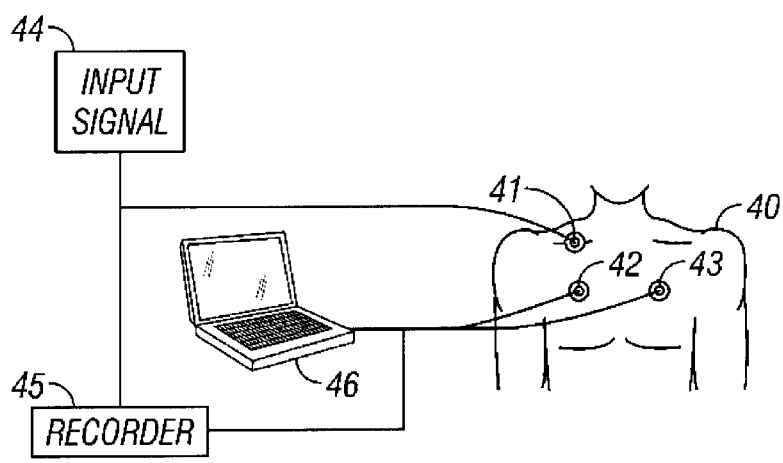
FIGS. 4a and 4b show embodiments of apparatus according to the invention when they are used on a human subject.

FIG. 4a shows an arrangement of the apparatus, of the invention on a human subject 40. An actuator 41 is placed near the clavicle and inputs a vibro-acoustic signal generated by input signal source 44. Impacting the chest wall skin over a rib or clavicular bony prominence will efficiently conduct excitation energy around the rib cage, thus coupling acoustic energy into the pneumothorax free air volume and excite its resonance behavior. Two transducers 42, 43 are placed below the actuator near the third rib for detecting the transmitted signal from actuator 41 through the thorax. The response signal generated by each transducer is sent to computer 46 where the signals are analyzed. A recorder 45 collects a record of the input signal and the detected response signals.

Figure 4B:
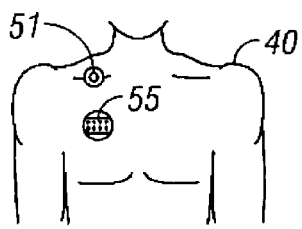

FIG. 4b shows an alternate embodiment of the invention used on a human subject. Handheld actuator 51 is placed on the clavicle for inputting a vibro-acoustic waves into the thorax. The transmitted waves are then detected at handheld unit 55. Handheld unit 55 includes a sensor with built-in microprocessor and display.

Figure 16:
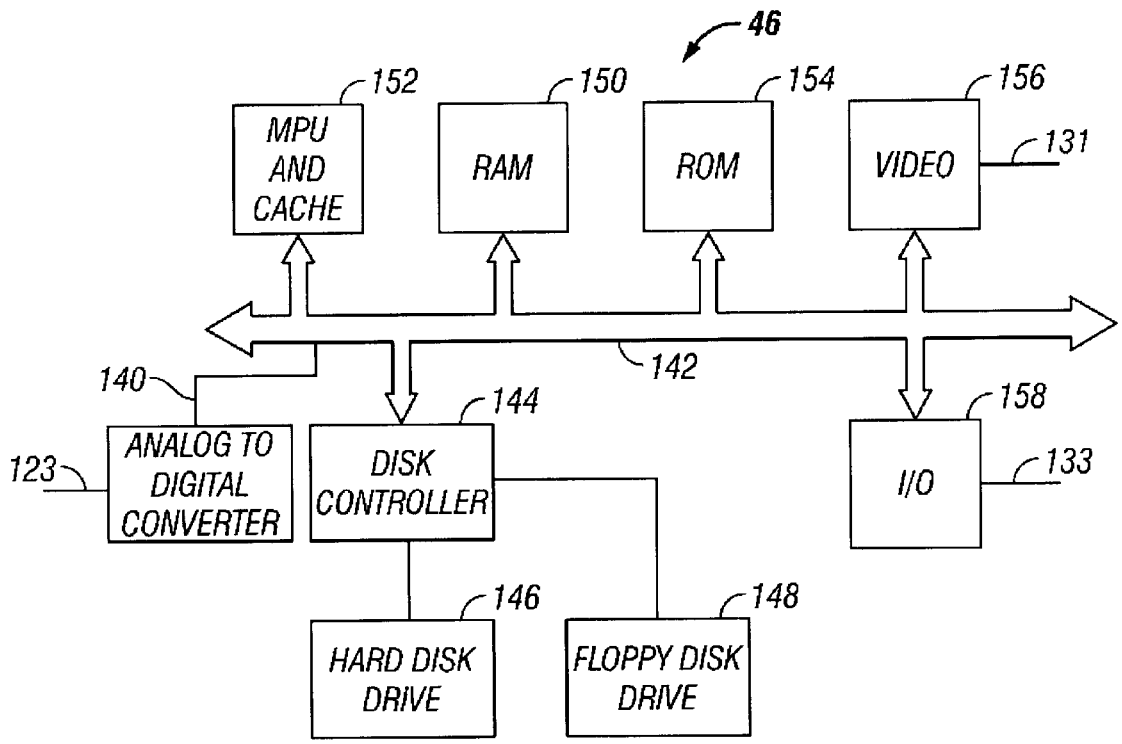

Referring now to FIG. 16, a block diagram of the computer 46 in FIG. 4a is shown therein. The computer 46 receives the analog vibro-acoustic wave signals on a line 123 at an analog digital converter. The vibro-acoustic wave signals are digitized and fed over lines 140 to a system bus 142 of the computer 46. The computer 46 includes a disk controller 144 having connected to it a hard disk drive 146 and a floppy disk drive 148. The hard disk drive 146 stores a program as represented by flow charts FIGS. 5 through 10 inclusive. Upon receipt of signals from the patient the selector routines are transferred from the hard disk drive 146 through the disk controller 144 to the system bus 142 and are loaded into random access memory 150 connected to the system bus for execution by a microprocessor 152. Portions of the code and data may be stored from time to time in a cache memory associated with the microprocessor. Read only memory 154 contains operating system information and outputs may be provided from the system bus by a video controller 156 to a video output line 131 connected to the display 132. Likewise, outputs may be connected through an input/output module having parallel and serial ports 158 through a line 133. The transducers as may best be seen in FIG. 4a, transducers 42 and 43 are placed on a torso 40 of a human being with the actuator 41 being placed near the clavicle to pick up vibro-acoustic waves for provision to the computer.

While a precise mechanical model of the abdominal cavity for vibro-acoustic study presently exits, the physical properties of the abdominal walls and other tissue can be approximated through various mixtures of agar, water, gel and other substances. The abdominal wall is made up of several structures, including skin, fat, muscle and peritoneum. With visceral perforation, extraluminal gas will rise to the most superior point given adequate time for gas migration. For supine patients, gas will collect between the abdominal viscera and the anterior abdominal wall. Considering external oscillatory excitation of the abdomen in the vertical direction, several types of mechanical waves, including compression, shear and surface, will radiate from the excitation source. The dominance and nature of the different types of waves is heavily dependent on the frequency. For example, at higher frequencies, such as those used in ultrasonic imaging techniques, e.g. order of MHz, shear waves and surface waves are rapidly attenuated as they propagate away from the excitation source. Compression waves, on the other hand, are not rapidly attenuated and have wavelengths of the order of internal organs. Hence, reflections off organ interfaces produce images. In the low frequency regime, e.g. below 2 kHz, shear and surface waves propagate more significant distances and compression waves have wavelengths on the order of meters. Consequently, for compression waves, a wave type analysis can be abandoned and a modal-based description, i.e. modeling the system dynamic response to excitation in terms of effective mass, stiffness and damping values, or impedance characteristics.

The abdominal cavity can be modeled by first assuming a homogeneous abdominal wall of uniform thickness and a hemispherical or domed shape. Then the intestinal region is replaced with a homogeneous medium representing its mean vibro-acoustic properties. Finally, the domed shape is replaced with a planar (circular) geometry. This simplified configuration has been solved by considering the problem of forced vibrations of a circular membrane with fixed boundary conditions. The membrane is backed by a medium that is uniform in the radial and angular directions with properties dependent on the extraluminal gas condition.

Several input signals were considered during the pilot study. White noise provided answers for a wide frequency range, but accuracy problems arise when the signal to noise ratio is low. Phase unwrapping is necessary for phase delay calculations. Pure tones work better under noisy conditions but provide results for each frequency separately. Phase delay estimation also needs an unwrapping algorithm. Amplitude modulation of pure tone bursts by using wave envelopes in signal-delay calculations can be used in place of unwrapping.

To provide broad frequency band excitation to ensure that air volume resonances are driven, a continuous random excitation source, a swept frequency source or a transient source, such as an impulse, discrete frequency or a chirp, may be employed. The advantage of a chirp signal is that it is well defined and may offer precise information in the time and frequency domains. Another advantage of impulse excitation is that it can be easily applied using an instrumented impact hammer with an impedance head mounting. However, there is less control over the level of vibratory energy input as a function of frequency. The advantage of a continuous random signal is that it is easier to implement. Both must be tailored to input energy into the frequency domain of interest where air volume resonances are expected. Different range settings may be selected to detect different size pneumothorax and pneumoperitoneum conditions.

A transfer function measurement of the ratio of sensor output to excitation input can be used to minimize chest wall dynamics contamination. Additionally, force and motion measurements at the point of excitation may also be taken. Knowledge of chest wall impedance conditions can be used in the diagnosis as well as in filtering out non-diagnostic localized chest wall dynamics. Static pressure of application of the actuator and sensor may be monitored with a load cell (see FIG. 3b) to take into account any affect on the response measurements.

Various air coupled and contact sensors or transducers as well as optical sensors may be used. For optimal coupling to the skin's surface, the measurement sensor's dynamic impedance should match that of the skin surface. The sensor should also have high signal-to-noise ratio, high sensitivity and good ambient noise shrouding capability. Two air coupled microphones (Radio Shack, Fort Worth, Tex. and Labtron, Hauppage, N.Y.) and two contact sensors (MCG, Branford, Conn. and Siemens, Iselin, N.J.) were identified and used. A low-pass filter can be used to avoid aliasing and remove high frequency noise. Preliminary tests indicate that the phase of the air coupled microphones are sensitive to static pressure between the sensor and the patient.

Figure 5:
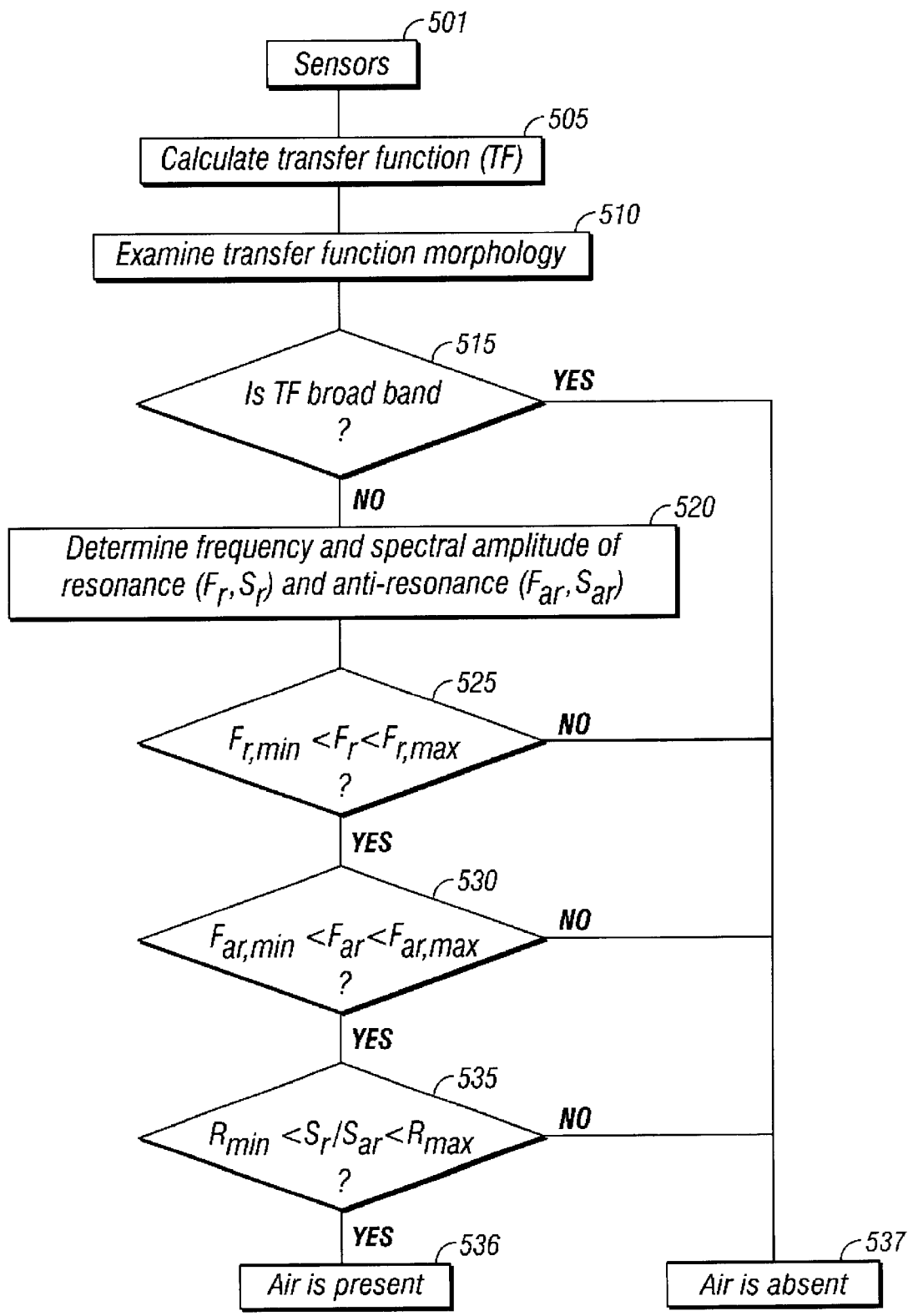
FIGS. 5 through 10 are flow charts of an exemplary method according to the invention.

A method according to the invention is shown in FIGS. 5 through 10. The subject to be examined will generally be in a supine position. An actuator is then positioned at the skin surface, preferably on a rib or clavicular bony prominence and acoustic excitation introduced into the thorax. Referring to FIG. 5, in step 501, one or more sensors are then placed in appropriate locations on the subject. As noted above, preferably the sensors are positioned about the suspected pneumothorax or pneumoperitoneum and with respect to the actuator to optimize detection. The static force of the actuator and sensors may also be monitored. A processor, such as a laptop computer, receives the signals from the sensors and calculates and displays the acoustic and physiologic (if physiologic monitoring is additionally present) changes in real time. All data is stored digitally. Acoustic data may be stored simultaneously in analog form on a 4-track or other audio recording medium for post processing and analysis.

Figure 6:
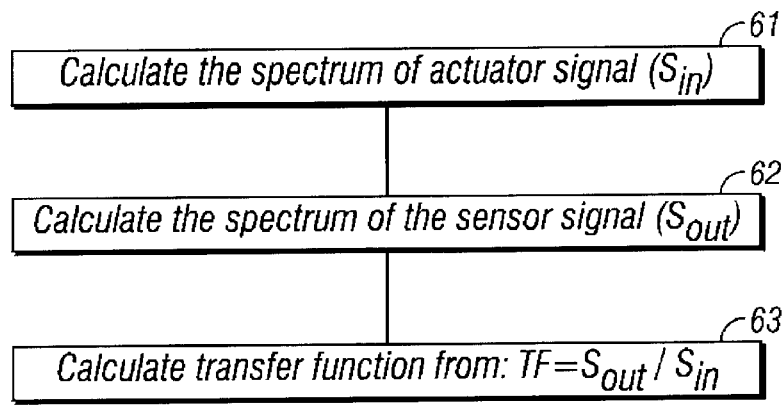

Step 505 is the-calculation of the transfer function, TF. Referring to FIG. 6, the transfer function is calculated by first calculating the spectrum of the actuator signal, Sin, in step 61. Then the spectrum of the sensor signal is calculated, $S_{out}$ step 62. Preferably, the auto spectrum of $S_{in}$ and $S_{out}$ is calculated using a commercial software package (LABVIEW by National Instruments, Austin, Tex.) using fast Fourier transforms. Finally, transfer function is calculated by taking the ratio of $S_{out}$ to $S_{in}$.

Figure 7:
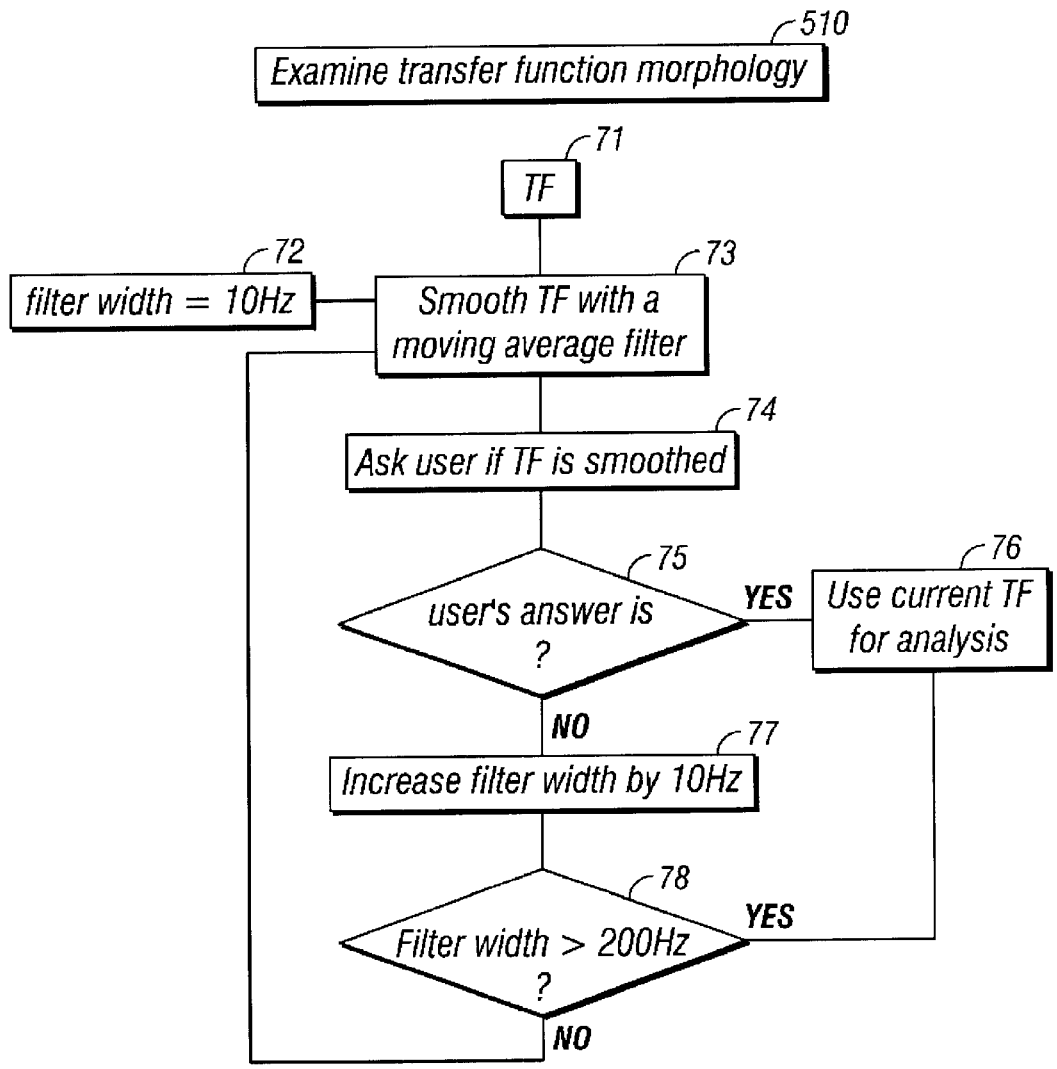
Figure 8:
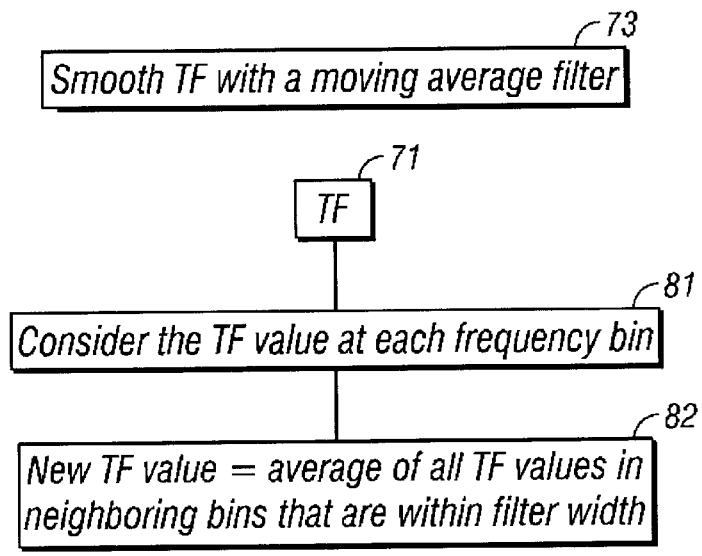

After the transfer function is calculated, it's morphology is examined (step 510). Referring to FIG. 7, the transfer function is first smoothed with a moving average filter (step 73). First, filter width is initially set at 10 Hz. Then, the TF value is considered at each frequency bin (step 81 of FIG. 8). Then a new TF value is calculated as the average of all the TF values in neighboring bins that are within the filter width (step 82). Referring back to FIG. 7, at step 74, the user is asked if the TF is smoothed. If the answer is yes, step 76, then the user is directed to use the current value of TF for the analysis. If the answer is no, then the filter width is increased by 10 Hz (step 77). Filter width is checked to determine if it is greater than 200 Hz (step 78). If the answer is yes, use the current TF for analysis. If the answer is no, the smoothing step is repeated in step 73. The smoothing process continues to loop until either TF is smooth or filter width is greater than 200 Hz.

Figure 9:
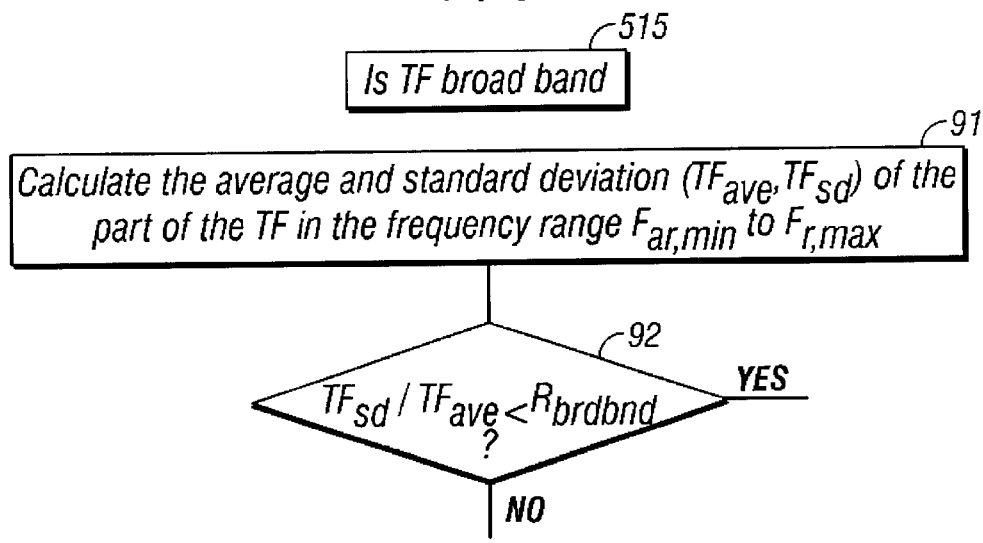

Once the transfer function is smoothed, the next step is to determine if the transfer function is broad band (step 515). Referring to FIG. 9, first the average and standard deviation of the transfer function ($TF_{ave}$, $TF_{sd}$) of the part of the transfer function in the frequency range Far,min to Far, max is calculated (step 91). Then the ratio of $TF_{sd}$ to $TF_{ave}$ is calculated. If it is less than a predetermined ratio, $R_{brdbnd}$ (step 92), then the transfer function is broad. If the transfer function is broad band, then air is absent (step 537). Otherwise, the method continues to step 520. Typical values of threshold settings are:

$F_{r,min}$=250 Hz $F_{r,max}$=750 Hz $F_{ar,min}=F_{r,min}/2$ $F_{ar,max}=F_{r,max}/2$ $R_{min}$=1.2

$R_{max}$=15

$R_{brdbnd}$=1.1

Figure 10:
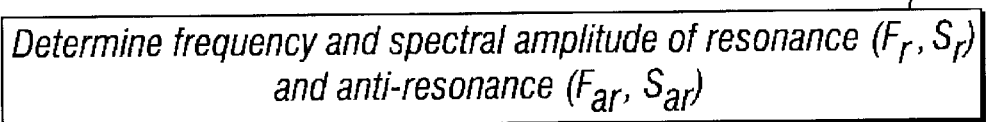

In step 520, the spectral frequency and spectral amplitude of the resonance ($F_r$, $S_r$) and the anti-resonance ($F_{ar}$, $S_{ar}$) is determined. Referring to FIG. 10, in step 101, $S_r$ is equal to the largest value of the transfer function for frequencies greater than 200 Hz. Fr is equal to the corresponding frequency. In step 102, $S_{ar}$ is equal to the smallest value of the transfer function for frequencies less than $F_r$. $F_{ar}$ is the corresponding frequency.

Then a series of tests are performed to determine if air is absent. In step 525, if the answer to the test $F_{r,min}<F_r<F_{r,max}$ is no, then air is absent. If the answer is yes, the method continues to step 530. If the answer to $F_{ar,min}<F_{ar}<F_{ar,max}$ is no, air is absent. If the answer is yes, the method continues to step 535. If the answer to $R_{min}<S_r/S_{ar}<R_{max}$ is no, then air is absent. If the answer is yes, then air is present (step 536).

Resonance and anti-resonance are determined using digital signal processing techniques. After the auto spectrum of $S_{in}$ and $S_{out}$ are calculated, the frequency response (FR) of the chest is determined from the equation FR=$S_{out}/S_{in}$. This calculation is repeated from 200 to 400 realizations. For a typical length of 50 ms/realization, a test period of 10–20 seconds will generally be required. Then the average and standard deviation of the FR is calculated for each frequency. Confidence limits at the 95% confidence levels assuming a normal distribution were determined. The limits are equal to the average plus or minus 1.96 times the standard deviation. Resonance and anti-resonance are then found by searching for maxima and minima in the FR (as mentioned above).

The basic difference in the morphology of the FR in the baseline and disease states is that the later has a resonance peak in the 400–700 Hz band, and an apparent anti-resonance at about half that frequency. Therefore, the ratio of the FR value at these extreme points may be chosen as a basic characteristic of interest. Statistical analyses were performed on tests of mongrel dogs.

Figure 11A:
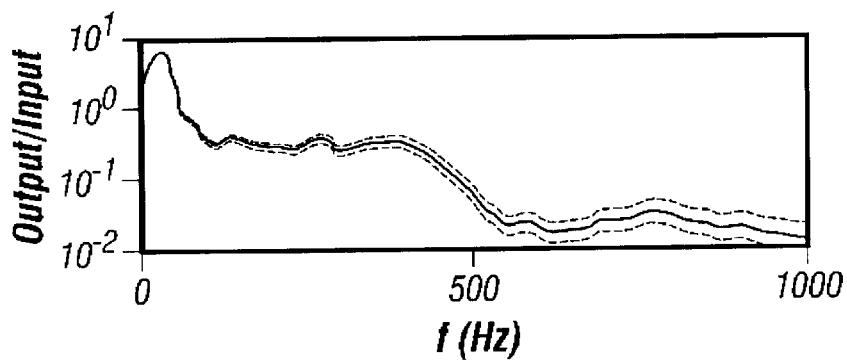
FIGS. 11a–15b show additional frequency response measurements of dogs during a pilot study.
Figure 11B:
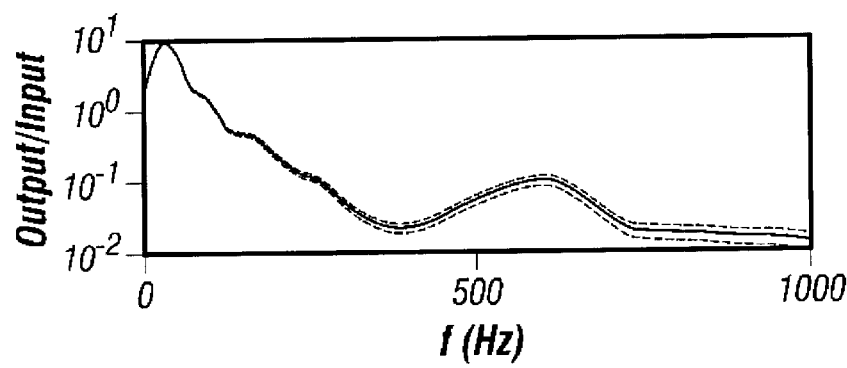
Figure 12A:
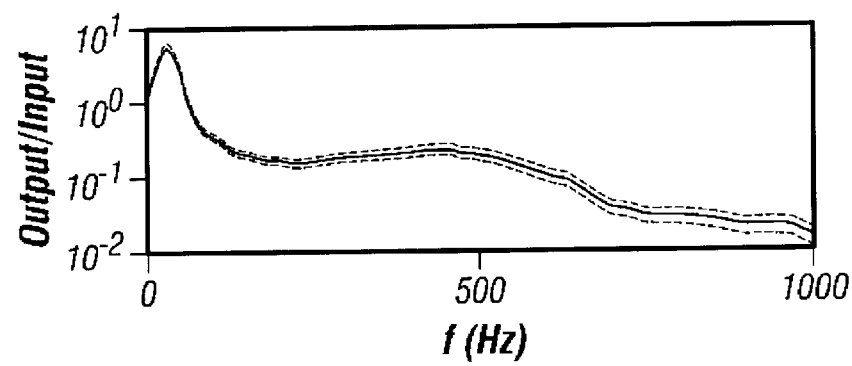
Figure 12B:
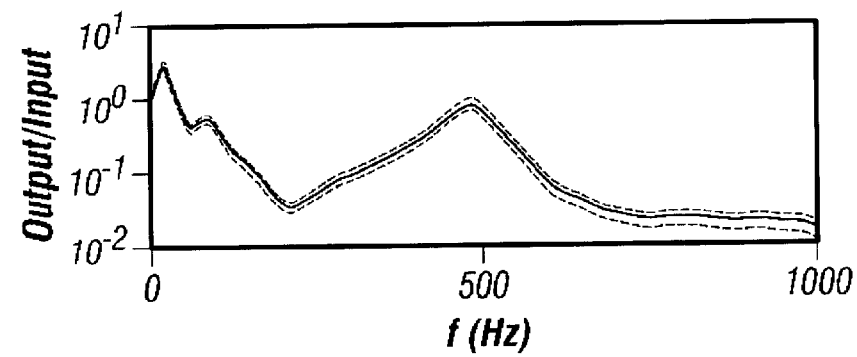
Figure 13A:
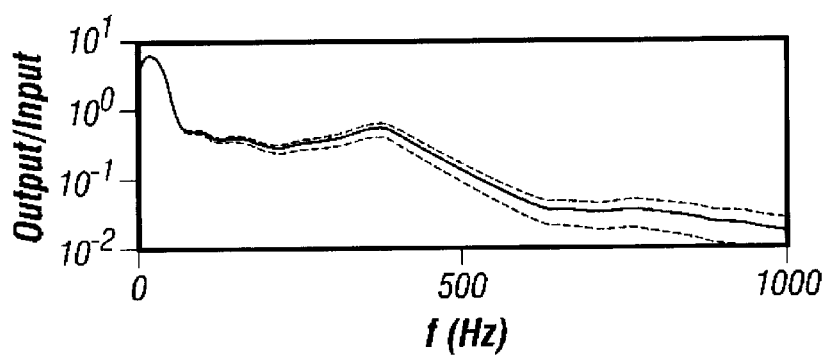
Figure 13B:
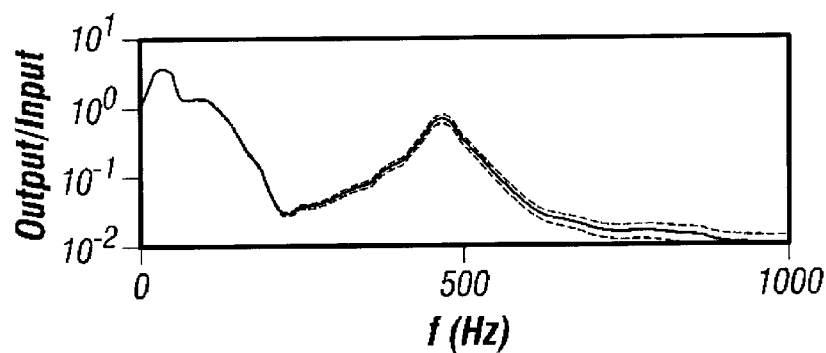
Figure 14A:
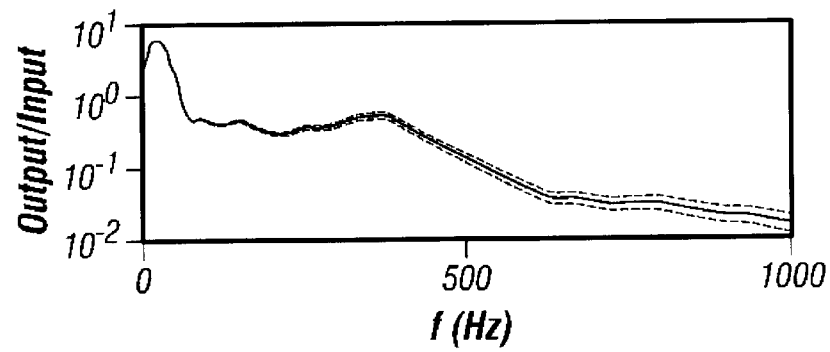
Figure 14B:
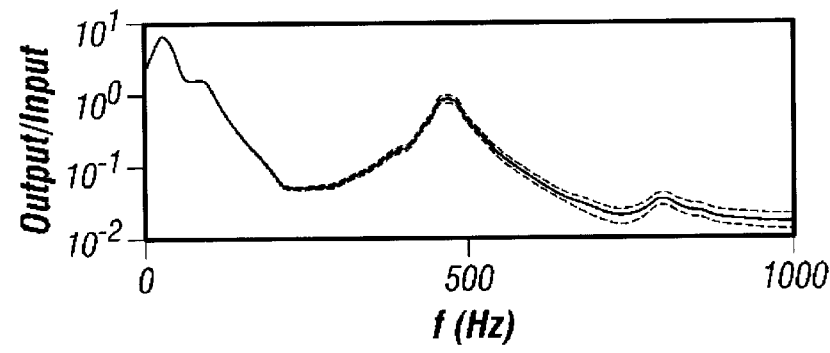
Figure 15A:
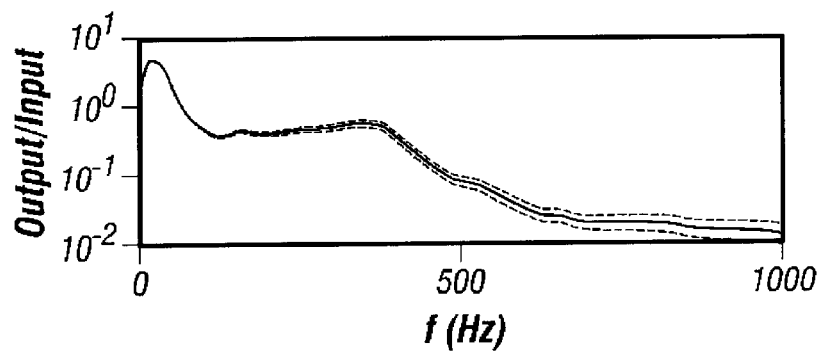
Figure 15B:
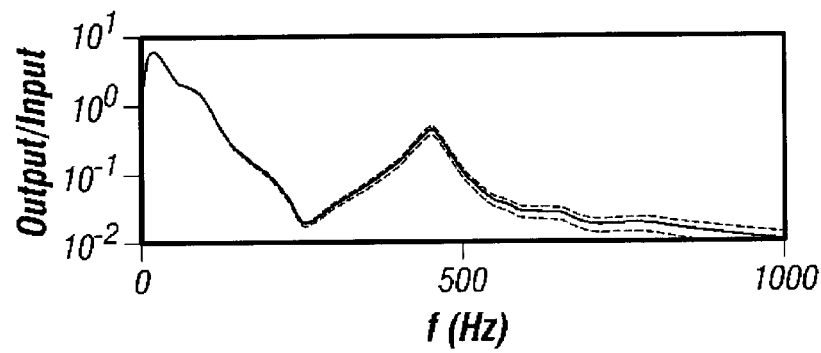

FIGS. 11a and 11b show the frequency response of dog 1 measured at the midline for the baseline 11a and the pneumoperitoneum 11b states with a solid line representing the mean and dashed lines representing the 95% confidence limits. FIGS. 12a and 12b, 13a and 13b for dogs 2 and 3. FIGS. 14a and 14b and 15a and 15b show frequency response of dog 3 measured 10 cm left of the midline and 20 cm left of the midline, respectively.

The spectra at the detection points were calculated and normalized by those of the input vibration (shaker output). The frequency-dependent response in each is clear. After an initial decrease in amplitude with increasing frequency, the amplitude reached a plateau (for f=70 400 Hz). Then it continued to-decrease for frequencies-greater than 400 Hz. Consistent spectral changes were detected when free gas was introduced.

Each vibro-acoustic data set was divided into 320 non-overlapping segments (62.5 ms each). The average and standard deviation of the FR was calculated for each 63 frequency bins (16 Hz resolution) from 0–1000 Hz. Using the ratio characteristic, the p-values of the FR differences between baseline and disease states were found to be 0.08, 0.001 and 0.00007 for the pilot dogs.

For simplified analysis, the air volume may be approximated by a gas bubble in a liquid medium. Fundamental resonant frequencies associated with bubble sizes ranging from 1 to 10 cm in diameter are estimated to be from 665 to 650 Hz. These estimates are likely low as the tissue mass surrounding the air volume presents less effective mass than that which is assumed in the crude calculation. Pilot studies have confirmed the order of magnitude accuracy and the bias of the theoretical prediction.

Initial testing shows that the apparatus and method of the invention will probably not replace CT, but may be equal to, or more sensitive than the commonly used plain film techniques in the detection of small to moderate volumes of pneumoperitoneum. This advantage is significant, especially when viewed from the point of the system's low cost and portability.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A method of detecting the presence of a gas cavity in a desired region of a body comprising the steps of:
   positioning a source of low frequency vibro-acoustic waves at a first location on the body;
   positioning a detector at a second location of the body;
   transmitting low frequency vibro-acoustic waves into the first location of the body;
   detecting the transmitted low frequency vibro-acoustic waves at the second location on the body;
   generating a signal representative of the frequency response of the body resulting from the presence of any gas cavity therein;
   analyzing the frequency response signal by calculating a transfer function of the frequency response signal and examining the transfer function morphology, wherein calculating the transfer function includes calculating the spectrum of the source of low frequency vibro-acoustic waves ($S_{in}$) and calculating the spectrum of the detected low frequency vibro-acoustic waves ($S_{out}$) wherein the transfer function is equal to the ration of $S_{in}$ to $S_{out}$; and
   detecting the presence of peaks in the response signal indicative of resonance waves and detecting the presence of dips in the response signal indicative of anti-resonance waves.

2. The method of claim 1 wherein the step of examining the transfer function includes the steps of:
   smoothing the transfer function with a moving average filter.

3. The method of claim 1 further comprising the step of determining the frequency and spectral amplitude of the resonance ($F_r$, $S_r$) and anti-resonance of the response signal ($F_{ar}$, $S_{ar}$).

4. The method of claim 3 further comprising the step of determining if $F_r$ is between a predetermined minimum and maximum value.

5. The method of claim 3 further comprising the step of determining if $F_{ar}$ is between a predetermined minimum and maximum value.

6. The method of claim 3 further comprising the step of determining if the ratio of $S_r/S_{ar}$ is between a predetermined minimum and maximum value.

7. The method of claim 1 further comprising the step of positioning the detector at a third location to enhance the resonance portion of the response signal and to diminish the anti-resonance portion of the response signal.

8. A method of detecting the presence of a gas cavity in a desired region of a body comprising the steps of:
   positioning a source of low frequency vibro-acoustic waves at a first location on the body;
   positioning a detector at a second location of the body;
   transmitting low frequency vibro-acoustic waves into the first location of the body;
   detecting the transmitted low frequency vibro-acoustic waves at the second location on the body;
   generating a signal representative of the frequency response of the body resulting from the presence of any gas cavity therein;
   analyzing the frequency response signal by calculating a transfer function of the frequency response signal and examining the transfer function morphology, wherein examining the transfer function includes smoothing the transfer function with a moving average filter; and
   detecting the presence of peaks in the response signal indicative of resonance waves and detecting the presence of dips in the response signal indicative of anti-resonance waves.

9. The method of claim 8 further comprising the step of determining the frequency and spectral amplitude of the resonance ($F_r$, $S_r$) and anti-resonance of the response signal ($F_{ar}$, $S_{ar}$).

10. The method claim 9 further comprising the step of determining if $F_r$ is between a predetermined minimum and maximum value.

11. The method of claim 9 further comprising the step of determining if $F_{ar}$ is between a predetermined minimum and maximum value.

12. The method of claim 9 further comprising the step of determining if the ration of $S_r/S_{ar}$ is between a predetermined minimum and maximum value.

13. The method of claim 8 further comprising the step of positioning the detector at a third location to enhance the resonance portion of the response signal and to diminish the anti-resonance portion of the response signal.

14. A method of detecting the presence of a gas cavity in a desired region of a body comprising the steps of:

positioning a source of low frequency vibro-acoustic waves at a first location on the body;

positioning a detector at a second location of the body;

transmitting low frequency vibro-acoustic waves into the first location of the body;

detecting the transmitted low frequency vibro-acoustic waves at the second location on the body;

generating a signal representative of the frequency response of the body resulting from the presence of any gas cavity therein;

analyzing the frequency response signal by calculating a transfer function of the frequency response signal and examining the transfer function morphology;

detecting the presence of peaks in the response signal indicative of resonance waves and detecting the presence of dips in the response signal indicative of anti-resonance waves; and determining the frequency and spectral amplitude of the resonance ($F_r$, $S_r$) and anti-resonance of the response signal ($F_{ar}$, $S_{ar}$).

15. The method of claim 14 wherein the step of examining the transfer function includes the steps of:

smoothing the transfer function with a moving average filter.

16. The method of claim 14 further comprising the step of determining if $F_r$ is between a predetermined minimum and maximum value.

17. The method of claim 14 further comprising the step of determining if $F_{ar}$ is between a predetermined minimum and maximum value.

18. The method of claim 14 further comprising the step of determining if the ratio of $S_r/S_{ar}$ is between a predetermined minimum and maximum value.

19. The method of claim 14 further comprising the step of positioning the detector at a third location to enhance the resonance portion of the response signal and to diminish the anti-resonance portion of the response signal.

* * * * *

UNITED STATES PATENT AND TRADEMARK OFFICE
CERTIFICATE OF CORRECTION

PATENT NO.    : 6,595,928 B2  
DATED         : July 22, 2003  
INVENTOR(S)   : Mansy et al.

It is certified that error appears in the above-identified patent and that said Letters Patent is hereby corrected as shown below:

Column 10,
Line 3, change "($S_{out}$)" to -- ($S_{out}$), --.
Line 62, change "ration" to -- ratio --.

Signed and Sealed this

Twenty-eighth Day of October, 2003

JAMES E. ROGAN
*Director of the United States Patent and Trademark Office*